United States Patent [19]

Balkovec et al.

[11] Patent Number: 5,348,940
[45] Date of Patent: Sep. 20, 1994

[54] CYCLOHEXAPEPTIDYL HYDROXYPROPIONITRILE COMPOUNDS

[75] Inventors: James M. Balkovec, North Plainfield; Robert A. Zambias, Springfield, both of N.J.

[73] Assignee: Merck & Co., Inc., Rahway, N.J.

[21] Appl. No.: 936,434

[22] Filed: Sep. 3, 1992

Related U.S. Application Data

[63] Continuation-in-part of Ser. No. 771,018, Oct. 1, 1991, abandoned.

[51] Int. Cl.$^5$ .................. A61K 37/02; C07K 7/50
[52] U.S. Cl. .................. 514/11; 514/2; 514/9; 530/317; 530/318; 930/190; 930/200; 930/270; 930/DIG. 546; 435/71.3; 435/71.1
[58] Field of Search ............ 514/11, 9, 2; 530/317, 530/318; 930/190, 200, 270, DIG. 546; 435/71.3, 71.1

[56] References Cited

U.S. PATENT DOCUMENTS

| | | | |
|---|---|---|---|
| 4,173,629 | 11/1979 | Dreyfuss et al. | 530/317 |
| 4,287,120 | 9/1981 | Abbott et al. | 530/317 |
| 4,293,485 | 10/1981 | Debono | 530/317 |
| 4,293,489 | 10/1981 | Debono | 530/317 |
| 4,320,054 | 3/1982 | Abbott et al. | 530/317 |
| 4,931,352 | 6/1990 | Fromtling et al. | 435/71.3 |
| 4,968,608 | 11/1990 | Giacobbe et al. | 435/71.1 |
| 5,021,341 | 6/1991 | Giacobbe et al. | 435/71.1 |
| 5,021,403 | 6/1991 | Sesin et al. | 514/9 |

FOREIGN PATENT DOCUMENTS

0405997A1 3/1990 European Pat. Off.
0486011A2 5/1992 European Pat. Off.

OTHER PUBLICATIONS

Pache et al, 13th ICC (1983), PS 4.8/3.
Kurokawa, et al, N.J. Am. Chem. Soc. 108, pp. 6043-6045.
Merck Manual of Diagnosis and Therapy, 11th Ed., pp. 885-891.
Balkovec, J., Chem. Abstr. 116, (1991) #129638g.
Balkovec, J. Chem. Abstr. 116, (1991) #129636e.

Primary Examiner—Merrell C. Cashion, Jr.
Assistant Examiner—T. D. Wessendorf
Attorney, Agent, or Firm—Mark Daniel; Elliott Korsen

[57] ABSTRACT

Certain propionitrile compounds which have a cyclohexapeptidyl nucleus and which are found to have antibiotic activity with physical properties suitable for use in therapeutic compositions are described. A novel process for their preparation is also described.

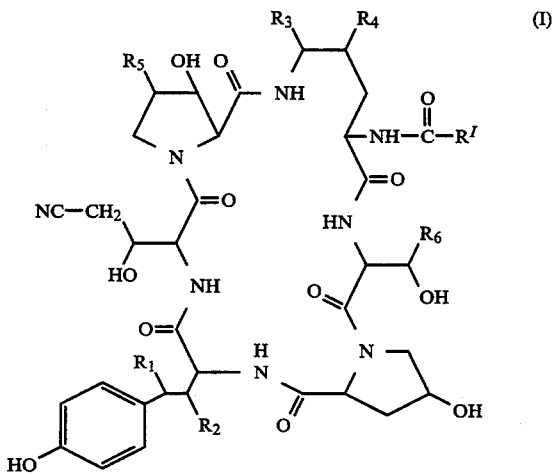

9 Claims, No Drawings

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:

(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 1:

```
Xaa Thr Xaa Xaa Xaa Xaa
 1               5
```

(2) INFORMATION FOR SEQ ID NO:2:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 2:

```
Xaa Thr Xaa Xaa Xaa Xaa
 1               5
```

(2) INFORMATION FOR SEQ ID NO:3:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 3:

```
Xaa Ser Xaa Xaa Xaa Xaa
 1               5
```

(2) INFORMATION FOR SEQ ID NO:4:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 4:

```
Xaa Thr Xaa Xaa Xaa Xaa
 1               5
```

(2) INFORMATION FOR SEQ ID NO:5:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 5:

```
Xaa Thr Xaa Xaa Xaa Xaa
 1               5
```

( 2 ) INFORMATION FOR SEQ ID NO:6:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 6:

Xaa  Thr  Xaa  Xaa  Xaa  Xaa
        1                      5

( 2 ) INFORMATION FOR SEQ ID NO:7:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 7:

Xaa  Thr  Xaa  Xaa  Xaa  Xaa
        1                      5

( 2 ) INFORMATION FOR SEQ ID NO:8:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 8:

Xaa  Thr  Xaa  Xaa  Xaa  Xaa
        1                      5

( 2 ) INFORMATION FOR SEQ ID NO:9:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 9:

Xaa  Thr  Xaa  Xaa  Xaa  Xaa
        1                      5

( 2 ) INFORMATION FOR SEQ ID NO:10:

( i ) SEQUENCE CHARACTERISTICS:
        ( A ) LENGTH: 6
        ( B ) TYPE: AMINO ACID
        ( C ) STRANDEDNESS: Not Relevant
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 10:

Xaa  Ser  Xaa  Xaa  Xaa  Xaa (2) INFORMATION FOR SEQ ID NO:11:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 11:

Xaa  Ser  Xaa  Xaa  Xaa  Xaa
        1                          5

(2) INFORMATION FOR SEQ ID NO:12:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 12:

Xaa  Thr  Xaa  Xaa  Xaa  Xaa
        1                          5

(2) INFORMATION FOR SEQ ID NO:13:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 13:

Xaa  Thr  Xaa  Xaa  Xaa  Xaa
        1                          5

(2) INFORMATION FOR SEQ ID NO:14:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 14:

Xaa  Thr  Xaa  Xaa  Xaa  Xaa
        1                          5

(2) INFORMATION FOR SEQ ID NO:15:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE ( x i ) SEQUENCE DESCRIPTION: SEQ ID NO: 15:

Xaa Thr Xaa Xaa Xaa Xaa
1               5

( 2 ) INFORMATION FOR SEQ ID NO:16:

( i ) SEQUENCE CHARACTERISTICS:
      ( A ) LENGTH: 6
      ( B ) TYPE: AMINO ACID
      ( C ) STRANDEDNESS: Not Relevant
      ( D ) TOPOLOGY: CIRCULAR ( i i ) MOLECULE TYPE:
      ( A ) DESCRIPTION: PEPTIDE ( x i ) SEQUENCE DESCRIPTION: SEQ ID NO: 16:

Xaa Ser Xaa Xaa Xaa Xaa
1               5

( 2 ) INFORMATION FOR SEQ ID NO:17:

( i ) SEQUENCE CHARACTERISTICS:
      ( A ) LENGTH: 6
      ( B ) TYPE: AMINO ACID
      ( C ) STRANDEDNESS: Not Relevant
      ( D ) TOPOLOGY: CIRCULAR ( i i ) MOLECULE TYPE:
      ( A ) DESCRIPTION: PEPTIDE ( x i ) SEQUENCE DESCRIPTION: SEQ ID NO: 17:

Xaa Thr Xaa Xaa Xaa Xaa
1               5

( 2 ) INFORMATION FOR SEQ ID NO:18:

( i ) SEQUENCE CHARACTERISTICS:
      ( A ) LENGTH: 6
      ( B ) TYPE: AMINO ACID
      ( C ) STRANDEDNESS: Not Relevant
      ( D ) TOPOLOGY: CIRCULAR ( i i ) MOLECULE TYPE:
      ( A ) DESCRIPTION: PEPTIDE ( x i ) SEQUENCE DESCRIPTION: SEQ ID NO: 18:

Xaa Thr Xaa Xaa Xaa Xaa
1               5

( 2 ) INFORMATION FOR SEQ ID NO:19:

( i ) SEQUENCE CHARACTERISTICS:
      ( A ) LENGTH: 6
      ( B ) TYPE: AMINO ACID
      ( C ) STRANDEDNESS: Not Relevant
      ( D ) TOPOLOGY: CIRCULAR ( i i ) MOLECULE TYPE:
      ( A ) DESCRIPTION: PEPTIDE ( x i ) SEQUENCE DESCRIPTION: SEQ ID NO: 19:

Xaa Thr Xaa Xaa Xaa Xaa
1               5

( 2 ) INFORMATION FOR SEQ ID NO:20:

( i ) SEQUENCE CHARACTERISTICS:
      ( A ) LENGTH: 6
      ( B ) TYPE: AMINO ACID
      ( C ) STRANDEDNESS: Not Relevant
      ( D ) TOPOLOGY: CIRCULAR (i i) MOLECULE TYPE:
         (A) DESCRIPTION: PEPTIDE (x i) SEQUENCE DESCRIPTION: SEQ ID NO: 20:

Xaa  Thr  Xaa  Xaa  Xaa  Xaa
         1                   5

(2) INFORMATION FOR SEQ ID NO:21:

(i) SEQUENCE CHARACTERISTICS:
         (A) LENGTH: 6
         (B) TYPE: AMINO ACID
         (C) STRANDEDNESS: Not Relevant
         (D) TOPOLOGY: CIRCULAR (i i) MOLECULE TYPE:
         (A) DESCRIPTION: PEPTIDE (x i) SEQUENCE DESCRIPTION: SEQ ID NO: 21:

Xaa  Thr  Xaa  Xaa  Xaa  Xaa
         1                   5

(2) INFORMATION FOR SEQ ID NO:22:

(i) SEQUENCE CHARACTERISTICS:
         (A) LENGTH: 6
         (B) TYPE: AMINO ACID
         (C) STRANDEDNESS: Not Relevant
         (D) TOPOLOGY: CIRCULAR (i i) MOLECULE TYPE:
         (A) DESCRIPTION: PEPTIDE (x i) SEQUENCE DESCRIPTION: SEQ ID NO: 22:

Xaa  Thr  Xaa  Xaa  Xaa  Xaa
         1                   5

(2) INFORMATION FOR SEQ ID NO:23:

(i) SEQUENCE CHARACTERISTICS:
         (A) LENGTH: 6
         (B) TYPE: AMINO ACID
         (C) STRANDEDNESS: Not Relevant
         (D) TOPOLOGY: CIRCULAR (i i) MOLECULE TYPE:
         (A) DESCRIPTION: PEPTIDE (x i) SEQUENCE DESCRIPTION: SEQ ID NO: 23:

Xaa  Ser  Xaa  Xaa  Xaa  Xaa
         1                   5

(2) INFORMATION FOR SEQ ID NO:24:

(i) SEQUENCE CHARACTERISTICS:
         (A) LENGTH: 6
         (B) TYPE: AMINO ACID
         (C) STRANDEDNESS: Not Relevant
         (D) TOPOLOGY: CIRCULAR (i i) MOLECULE TYPE:
         (A) DESCRIPTION: PEPTIDE (x i) SEQUENCE DESCRIPTION: SEQ ID NO: 24:

Xaa  Ser  Xaa  Xaa  Xaa  Xaa
         1                   5

(2) INFORMATION FOR SEQ ID NO:25:

(i) SEQUENCE CHARACTERISTICS:
         (A) LENGTH: 6
         (B) TYPE: AMINO ACID (C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 25:

```
Xaa Thr Xaa Xaa Xaa Xaa
 1               5
```

(2) INFORMATION FOR SEQ ID NO:26:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 26:

```
    Xaa Thr Xaa Xaa Xaa Xaa
 1   5
```

(2) INFORMATION FOR SEQ ID NO:27:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 27:

```
Xaa Thr Xaa Xaa Xaa Xaa
 1   5
```

(2) INFORMATION FOR SEQ ID NO:28:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 28:

```
Xaa Thr Xaa Xaa Xaa Xaa
 1   5
```

(2) INFORMATION FOR SEQ ID NO:29:

(i) SEQUENCE CHARACTERISTICS:
(A) LENGTH: 6
(B) TYPE: AMINO ACID
(C) STRANDEDNESS: Not Relevant
(D) TOPOLOGY: CIRCULAR (ii) MOLECULE TYPE:
(A) DESCRIPTION: PEPTIDE (xi) SEQUENCE DESCRIPTION: SEQ ID NO: 29:

```
Xaa Thr Xaa Xaa Xaa Xaa
 1   5
```

(2) INFORMATION FOR SEQ ID NO:30:

(i) SEQUENCE CHARACTERISTICS:
   (A) LENGTH: 6
   (B) TYPE: AMINO ACID
   (C) STRANDEDNESS: Not Relevant
   (D) TOPOLOGY: CIRCULAR (ii) MOLECULE TYPE:
   (A) DESCRIPTION: PEPTIDE (xi) SEQUENCE DESCRIPTION: SEQ ID NO: 30:

Xaa Thr Xaa Xaa Xaa Xaa
 1   5

CYCLOHEXAPEPTIDYL HYDROXYPROPIONITRILE COMPOUNDS

This is a continuation-in-part of application Ser. No. 07/771,018, filed Oct. 1, 1991, now abandoned.

DESCRIPTION OF THE INVENTION

The present invention is directed to certain cyclohexapeptidyl propionitrile compounds having the formula

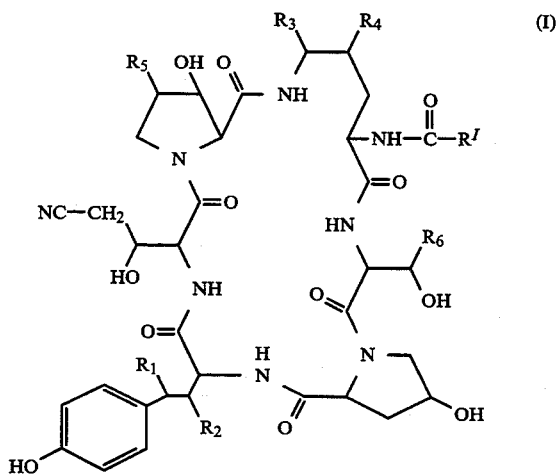

In the foregoing and succeeding formulas,
$R_1$ is H or OH
$R_2$ is H or OH
$R_3$ is H, OH or OR where R is $C_1$-$C_4$ alkyl or benzyl
$R_4$ is H or OH
$R_5$ is H, OH or $CH_3$
$R_6$ is H or $CH_3$, and
$R^I$ is $C_9$-$C_{21}$ alkyl, $C_9$-$C_{21}$ alkenyl, or $C_1$-$C_{10}$ alkoxyphenyl or $C_1$-$C_{10}$ alkoxynaphthyl.

Where the expression "alkyl", "alkenyl" or "alkoxy" is employed, it is intended to include branched as well as straight chain radicals.

Representative nuclei for the nitrile, Compound I, and the sequence ID for these compounds may be seen in the following table. Since the amino acid nuclei would be the same irrespective of substituent in the lipophilic side chain, the sequence identification number is assigned for the nuclear variation.

| NITRILE COMPOUND NUCLEI | $R_1$ | $R_2$ | $R_3$ | $R_4$ | $R_5$ | $R_6$ | SEQ. ID |
|---|---|---|---|---|---|---|---|
| I-1  | OH | OH | OH   | OH | H   | $CH_3$ | 1  |
| I-2  | OH | OH | OH   | OH | $CH_3$ | $CH_3$ | 2  |
| I-3  | H  | OH | OH   | OH | $CH_3$ | H   | 3  |
| I-4  | OH | H  | OH   | OH | $CH_3$ | $CH_3$ | 4  |
| I-5  | H  | H  | OH   | H  | $CH_3$ | $CH_3$ | 5  |
| I-6  | H  | H  | H    | H  | $CH_3$ | $CH_3$ | 6  |
| I-7  | OH | OH | H    | H  | $CH_3$ | $CH_3$ | 7  |
| I-8  | OH | OH | H    | H  | H   | $CH_3$ | 8  |
| I-9  | OH | OH | OH   | OH | OH  | $CH_3$ | 9  |
| I-10 | H  | OH | OH   | OH | H   | H   | 10 |
| I-11 | H  | OH | $OCH_3$ | OH | $CH_3$ | H   | 11 |
| I-12 | H  | OH | H    | OH | H   | $CH_3$ | 12 |
| I-13 | OH | OH | H    | OH | H   | $CH_3$ | 13 |
| I-14 | H  | OH | OH   | OH | H   | $CH_3$ | 27 |
| I-15 | OH | OH | $OCH_3$ | OH | H   | $CH_3$ | 28 |

Compounds which are particularly outstanding for the control of mycotic infections are Compound Ia (Seq. ID No. 1), Ib (Seq. ID. No. 12) and Ie (Seq. ID. No. 27) represented by the following formulas:

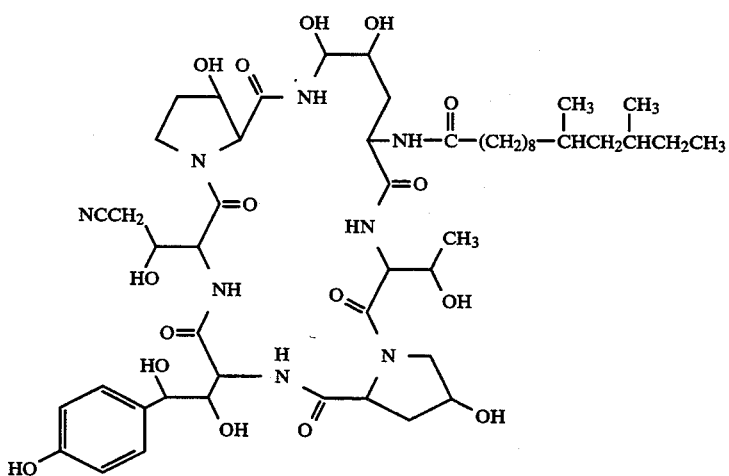

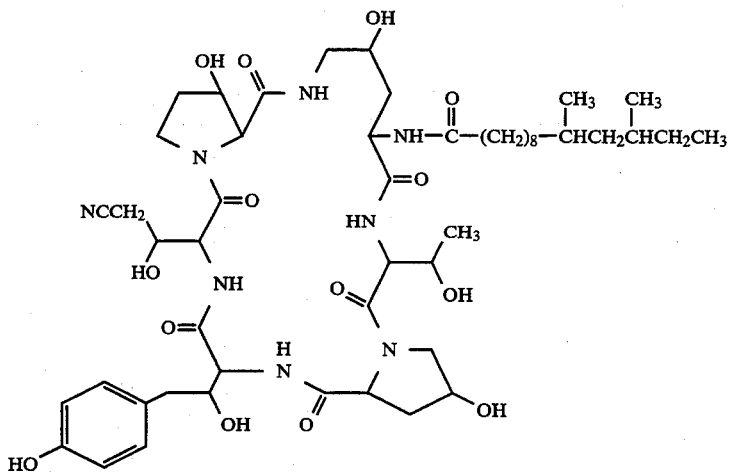

(Ib)

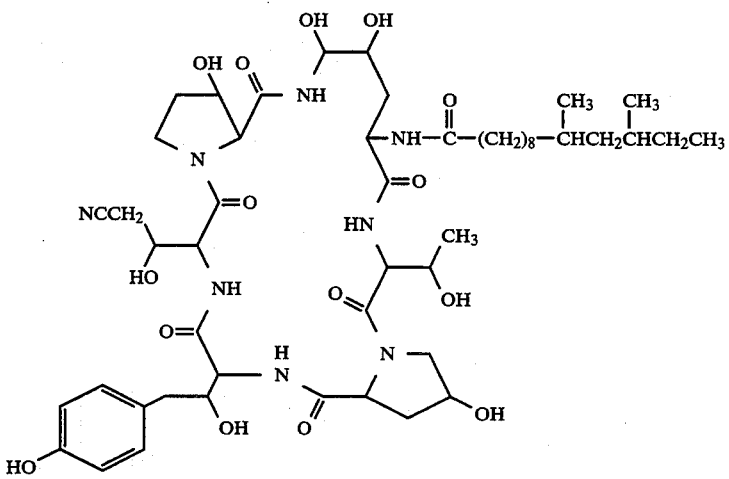

(Ie) Seq. ID. 27

The compounds are soluble in lower alcohols and polar aprotic solvents such as dimethylformamide (DMF) and pyridine, mixture of alkanol and water, polyethylene glycol and water, acetonitrile and water and the like. They are insoluble in solvents such as ether and acetonitrile.

The compounds of the present invention are useful as an antibiotic, especially as an antifungal agent. As antifungal agents they are useful for the control of both filamentous fungi and yeasts. They are especially adaptable to be employed for the treatment of mycotic infections in mammals, especially those caused by Candida species such as *C. albicans, C. tropicalis* and *C. pseudotropicalis*, as well as Aspergilli. They are also useful as intermediates for extremely active antifungal agents which have properties suitable for direct use and as intermediates for agents useful in the treatment and/or inhibition of *Pneumocystis carinii* pneumonia to which immune compromised patients are especially susceptible.

The compounds of the present invention may be prepared from a natural product or a derivative of a natural product. The nitrile may be represented by compounds of formula (I) (Seq. ID Nos. 1-13, 27 and 28) and the starting materials may be represented by compounds of formula (E) (Seq. ID Nos. 14-26, 29 and 30) as seen in the following diagrams:

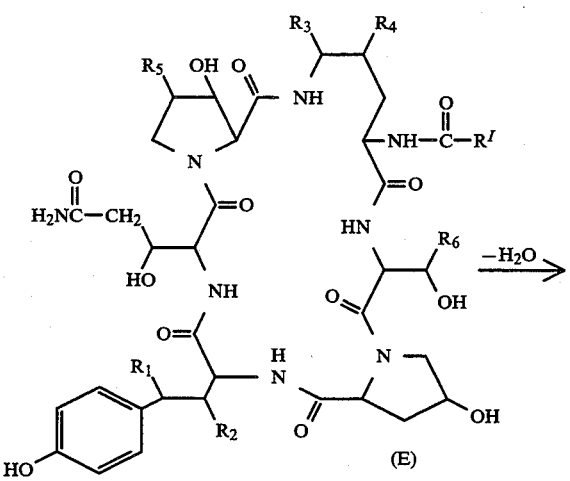

(E)

-continued

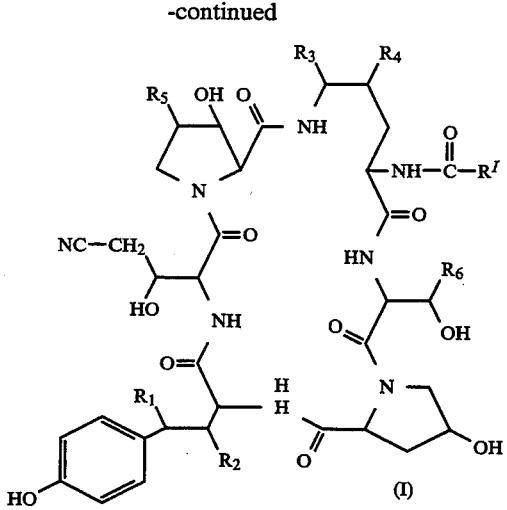

(I)

In certain cases, when a natural product with the corresponding nucleus is not known, the compound may be obtained by first preparing a closely related nitrile and thereafter modifying. Thus a compound with an I-14 nucleus may be obtained after first preparing a compound of I-1 nucleus and thereafter reducing $R_1$ from OH to H.

The nitriles (Compound I) are novel and useful compounds and are in addition, useful intermediates in the preparation of the amine compounds of the following formulas which are claimed in copending application: Ser. No. 07/771,017, filed Oct. 1, 1991, now abandoned in favor of continuation-in-part application Ser. No. 07/936,561, filed Sep. 3, 1992.

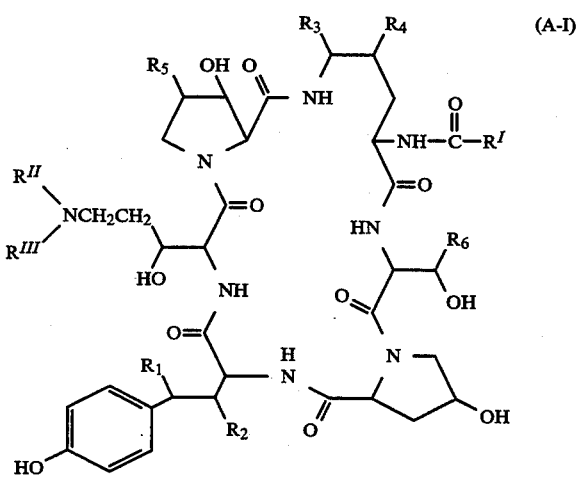

and

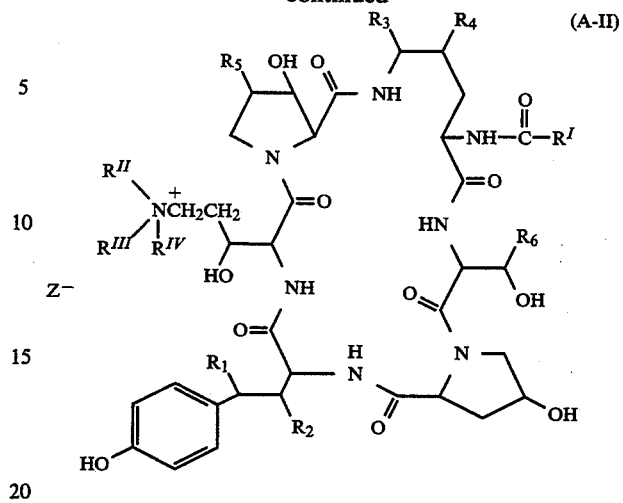

The starting materials for the nitriles are natural products or derivatives of natural products and are obtained from various sources and may be obtained as subsequently described.

The sequence identification numbers for the starting materials, Compound E (Seq. ID Nos. 14–26, 29 and 30), which correspond to the nitriles are seen below.

| STARTING MATERIAL | $R_1$ | $R_2$ | $R_3$ | $R_4$ | $R_5$ | $R_6$ | Seq. ID |
|---|---|---|---|---|---|---|---|
| E-1 | OH | OH | OH | OH | H | $CH_3$ | 14 |
| E-2 | OH | OH | OH | OH | $CH_3$ | $CH_3$ | 15 |
| E-3 | H | OH | OH | OH | $CH_3$ | H | 16 |
| E-4 | OH | H | OH | OH | $CH_3$ | $CH_3$ | 17 |
| E-5 | H | H | OH | H | $CH_3$ | $CH_3$ | 18 |
| E-6 | H | H | H | H | $CH_3$ | $CH_3$ | 19 |
| E-7 | OH | OH | H | H | $CH_3$ | $CH_3$ | 20 |
| E-8 | OH | OH | H | H | H | $CH_3$ | 21 |
| E-9 | OH | OH | OH | OH | OH | $CH_3$ | 22 |
| E-10 | H | OH | OH | OH | H | H | 23 |
| E-11 | H | OH | $OCH_3$ | OH | $CH_3$ | H | 24 |
| E-12 | H | OH | H | OH | H | $CH_3$ | 25 |
| E-13 | OH | OH | H | OH | H | $CH_3$ | 26 |
| E-14 | H | OH | OH | OH | H | $CH_3$ | 29 |
| E-15 | OH | OH | $OCH_3$ | OH | H | $CH_3$ | 30 |

The preparation of Compound I (Seq. ID Nos. 1–13, 27 and 28) may be carried out by the dehydration of the carboxamide group to the nitrile. When this method is employed the reaction is preferably carried out under nitrogen with cyanuric chloride in a solvent. It may be carried out in the presence of molecular sieves but if carried out in the absence of sieves, reaction time is critical, and usually order of addition becomes important. In the absence of sieves, or without careful control of reaction time, degradation may occur even when the $R_3$ hydroxyl is protected with an ether group.

Suitable reagents which may be employed in place of cyanuric chloride are anhydrides such as acetic anhydride, trifluoroacetic anhydride and phosphorus pentoxide; acid chlorides such as oxalyl chloride, phosphorus oxychloride, thionyl chloride, p-toluenesulfonyl chloride and chlorosulfonyl isocyanate; phosphonium reagents such as phosphorus pentachloride, triphenylphosphine/carbon tetrachloride, triphenylphosphonium ditriflate and triphenylphosphonium dichloride; carbodiimides such as dicyclohexylcarbodiimide; other dehydrating agents such as aluminum chloride, titanium tetrachloride, ethyl(carboxysulfamoyl)triethylammonium hydroxide and inner salt.

Suitable solvents include dimethylformamide or weakly basic solvents such as pyridine, collidine and the like.

Molecular sieves may be in the size range 3A to 5A.

The relative amounts of Compound E (Seq. ID Nos. 14–26, 29 and 30) and reagents vary, but in general the dehydrating agent is used in excess. From about 1.5 to 15 equivalents of the dehydrating agent are employed. The molecular sieves are used in amounts of 1 to 10 equivalents.

In carrying out the reaction using sieves, a suspension of molecular sieves in a rigorously dried solvent is first prepared, and while stirring under an atmosphere of nitrogen, there is added, cyanuric chloride or other dehydrating agent and thoroughly mixed. To the resulting mixture while stirring under an atmosphere of nitrogen is added the starting material, Compound E and the stirring continued for about 12 to 24 hours or until HPLC analysis of the reaction mixture indicates substantial completion of the reaction with the formation of the nitrile. The sieves are removed by filtration, preferably on a sintered glass funnel, and the filtrate concentrated and purified by preparative HPLC. The mobile phase used in the purification are varying ratios of a water/acetonitrile composition and an acetonitrile/water composition. These compositions are referred to in the examples as A and B. Composition A is 95/5 water/acetonitrile containing 0.1% trifluoroacetic acid (TFA) or acetic acid. Composition B is 95/5 acetonitrile/water containing 0.1% TFA or acetic acid. The exact mobile phase used for HPLC assays and the mobile phase used in preparative HPLCs may differ not only from each other but also from compound to compound but can be determined by the skilled artisan without difficulty.

In carrying out the reaction in the absence of sieves, solid cyanuric chloride is added in a single portion to a solution of Compound E in an aprotic solvent and stirred rapidly for a short time and the reaction mixture then quenched by adding aqueous sodium acetate directly to the reaction mixture. The volatiles are then removed in vacuo to obtain a solid residue which may be purified as above described.

When $R_1$ is H, $R_2$, $R_3$ and $R_4$ are OH, $R_5$ is H or $CH_3$ and $R_6$ is $CH_3$, the nitrile compound may be made using a nitrile compound, in which $R_1$ is OH with the remaining Rs being the same, and reducing it by methods known to the skilled in the art. Conveniently, this may be carried out by adding trifluoroacetic acid to the nitrile and sodium triacetoxyborohydride contained together and thereafter mixing until a clear solution is obtained and thereafter recovering the product as a precipitate by pouring into water. The precipitate product may then be purified by preparative HPLC by placing on the column in a methanol/water mixture and eluting with water/acetonitrile.

When $R_3$ is O-alkyl, the nitrile may be made using another nitrile compound in which $R_3$ is This may be accomplished by dissolving the nitrile compound in alkanol and adding an acid such as p-toluenesulfonic acid and stirring until the reaction is complete. The compound may be obtained by precipitation and purification as described above.

The compounds of the present invention are active against many fungi and particularly against Candida species. The antifungal properties may be illustrated with the minimum fungicidal concentration (MFC) determination against certain Candida and Cryptococcus organisms in a microbroth dilution assay carried out in a Yeast Nitrogen Base (Difco) medium with 1% dextrose (YNBD).

In a representative assay, Compound Ia was solubilized in 10% dimethyl sulfoxide (DMSO) and diluted to 2560 $\mu$g/ml. The solution was then diluted to 256 $\mu$g/ml in YNBD and dispensed via a multichannel pipetter into the top row of a 96-well plate (each well containing 0.15 ml of YNBD), resulting in a drug concentration of 128 $\mu$g/ml. Compounds in the top row were diluted 2-fold down the columns yielding final drug concentrations ranging from 0.06–128 $\mu$g/ml. All tests were performed in duplicate.

A four-hour broth culture of C. albicans MY 1055 was adjusted using a spectrophotometer at 530 nm to equal a 0.5 McFarland Standard. This yields a cell concentration of $1-5 \times 10^6$ colony forming units (CFU)/ml. The 96-well microplates were inoculated using an MIC-2000 (Dynatech), which delivers 1.5 $\mu$g per well, yielding a final inoculum per well of $1.5-7.5 \times 10^3$ cells. One column per tray containing drug-free growth control wells was included.

After 24 hours of incubation, the microtiter plates were shaken gently on a shaker to resuspend the cells. The MIC-2000 inoculator was used to transfer a 1.5 microliter sample from each well of the 96-well microtiter plate to a single reservoir inoculum plate containing Sabouraud dextrose agar (SDA). The inoculated SDA plates were incubated for 24 hours at 35° C. The results were as follows:

| Organism | | MFC $\mu$g/ml | |
|---|---|---|---|
| | | Compound Ia | Compound Ib |
| C. albicans | MY 1028 | 2 | 0.12 |
| C. albicans | MY 1055 | 2 | 1 |
| C. albicans | MY 1750 | 0.5 | 0.5 |
| C. tropicalis | MY 1012 | 0.125 | 0.5 |

For application in treating mycotic or Pneumocytis infections, a therapeutic amount of the compound of formula I is administered to a subject needing therapy. The exact amount depends on the compound, the organism, and the subject, and may be determined by the skilled in the art.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound I or one of the components. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound I with the components suitable for the medium desired. Compositions formulated for oral administration may be a liquid composition or a solid composition. For liquid preparations, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with lubricant such as calcium stearate, together with binders disintegrating agents and the like. Because of their ease in administration, tablets and capsules represent the most advantageous oral dosage form.

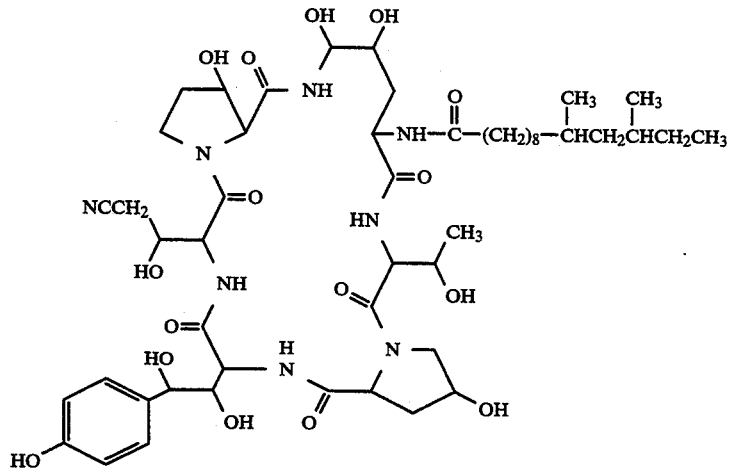

(Ia) Seq. ID No. 1

It is especially advantageous to formulate the compositions in unit dosage form (as hereinafter defined) for ease of administration and uniformity of dosage. Compositions in unit dosage form constitute an aspect of the present invention. Compositions may be formulated for injection and for injecton take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound also may be solubilized in alcohol/propylene glycol or polyethylene glycol for drip intravenous administration. These compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is for antifungal use any method of administration may be employed. For treating mycotic infections, oral administration is frequently preferred.

When the compound is to be employed for control of pneumocystis infections it is desirable to directly treat lung and bronchi. For this reason inhalation methods are preferred. For administration by inhalation, the compounds of the present invention are conveniently delivered in the form of an aerosol spray presentation from pressurized packs or nebulisers. The preferred delivery system for inhalation is a metered dose inhalation (MDI) aerosol, which may be formulated as a suspension or solution of Compound I in suitable propellants, such as fluorocarbons or hydrocarbons.

The following examples illustrate the invention but are not to be construed as limiting.

EXAMPLE I

Preparation of Nitrile Compound 550 milligrams (2.98 mmol; 1.5 molar eq) of cyanuric chloride was added to a suspension of 4A molecular sieves pre-prepared by stirring together 10.2 grams of 4A molecular sieves under nitrogen for 0.5 hour with 45 milliliters of DMF (predried over a combination of 13X and 3A molecular sieves), and the stirring continued for 5 minutes. To the resulting suspension was added 2.08 grams (1.95 mmol) of Compound E-1 (Seq. ID No. 14) ($R_1$, $R_2$, $R_3$ and $R_4$ are OH; $R_5$ is H; $R_6$ is $CH_3$; $R^I$ is 9,11-dimethyltridecyl). The resulting mixture still under nitrogen was then stirred for 18 hours. At the end of this period an HPLC analysis was carried out employing a "ZORBAX" (Dupont, 4.9 mm×25 cm) C8 column and eluting isocratically with 60/40 A:B (containing 0.1% TFA) at ambient temperature with detection by ultraviolet absorption at 210 nm which showed about a 2:1 ratio of product to starting material. The molecular sieves were filtered onto a sintered glass funnel and washed consecutively with 5 milliliters of DMF and 5 milliliters of methanol. The filtrate was concentrated in vacuo to a final volume of 20 milliters and filtered through a 0.45μ Whatman polypropylene syringe filter. The filtrate was diluted with mobile phase 65/35 A:B to a volume of 40 milliliters and pump injected at 10 milliliters per minute onto a Waters 45 mm ID radial compression column packed with 15μ, 100 Angstrom Δ-Pak C18 stationary phase. The column was eluted initially at 20 mL/min and the elution continued until the front running impurities had been eluted. The composition of the eluting agent was then stepped to 60/40 A:B and the flow increased to 40 mL/min. Fractions containing the desired product were pooled and concentrated in vacuo to remove most of the acetonitrile. The residue was lyophilized to obtain 800 milligrams (40 percent yield) of the nitrile (Seq. ID No. 1). The compound had the following spectral characteristics.

$^1$H-NMR (400 MHz, CD$_3$OD): δ 7.12 (d, 2H), 6.73 (d, 2H), 5.31 (d, 1H), 1.20 (d, 3H), 0.88 (t, 3H), 0.87 (d, 6H)

Mass spectra (FAB): 1054 (M+Li)

EXAMPLE II

Compound Ia of Example I may be prepared in the absence of sieves. In such an operation, 1.0 gram of Compound E-1 was placed in 12.0 milliliters of dry DMF at 17° C. and stirred rapidly. Solid cyanuric chloride (0.26 g, 1.4 mmol) then was added in a single portion and the mixture was stirred for exactly 5.5 minutes. The reaction mixture was then quenched with 4.2 mL aqueous 1M sodium acetate. The volatiles were removed in vacuo to obtain a solid. HPLC analysis 45/55 A:B (0.1% TFA) on "ZORBAX" C8 indicated 82 percent of the product was the desired nitrile. The nitrile may be purified as in Example I or by pouring a concentrated methanolic solution of the residue into dry acetonitrile, collecting the precipitate, and repeating the precipitation, this time from water, then collecting the solid and dissolving in methanol followed by removing the volatiles to obtain a granular solid.

EXAMPLE III phase (50/50 A:B) and filtered through a 0.45μ Whatman polypropylene syringe filter and injected onto a Waters 45 mm I.D. radial compression column packed with 15μ, 100A Δ-Pack C18 stationary phase. The desired fractions were combined and lyophilized to obtain 670 milligrams (34 percent) of nitrile, (Seq. ID No. 12) having a HPLC retention time of 8.0 min on a "ZORBAX" column when eluted isocratically with 45/55 A:B at 1.5 mL/min at 40° C.; detection at λ=210 nm.

$^1$H-NMR (400 MHz, CD$_3$OD): δ 7.00 (d, 2H), 6.70 (d, 2H), 5.02 (d, 1H), 4.98 (d, 1H), 1.20 (d, 3H), 0.89 (t, 3H), 0.86 (d, 6H)

Mass spectra (FAB): 1020 (M+Li)

EXAMPLE IV 250 milligrams (0.242 mmole) of the lipopeptide Compound E-12 (R$_1$ and R$_3$ are H, R$_2$ and R$_4$ are OH; R$_5$ is H; R$_6$ is CH$_3$; R$^I$ is 9,11-dimethyltridecyl; Seq. ID No. 25) was dissolved in 3 milliliters of dry pyridine and cooled to 0° C. Trifluoroacetic anhydride (0.36 mL, 2.5 mmol) was added in five portions. The starting lipopeptide was consumed at this point as determined by analytical HPLC (50/50 H$_2$O:CH$_3$CN), 2 ml/min, "ZORBAX" C8 column, λ=210, 277 nm). The reaction was

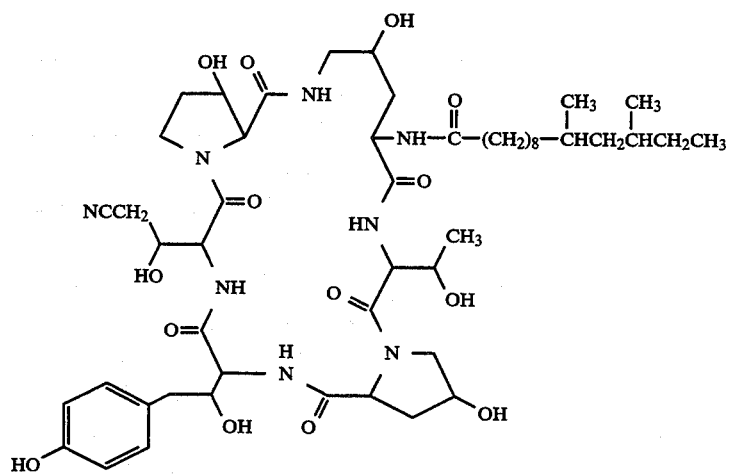

(Ib) Seq. ID No. 12

Preparation of Nitrile Compound

In an operation carried out in a manner similar to that described in Example I, 290 milligrams (1.57 mmol) of cyanuric chloride was added to a solution of 2.0 grams (1.94 mmol) of Compound E-12 (Seq. ID No. 25) (R$_1$ and R$_3$=H; R$_2$ and R$_4$=OH; R$_5$=H; R$_6$=CH$_3$; R$^I$ is 9,10-dimethyltridecyl) in 8.0 milliters of DMF and the reaction mixture stirred under nitrogen for 24 hours. At this time, an additional 290 milligrams (1.57 mmol) was added and the reaction continued for one hour whereupon the reaction was judged complete by HPLC "ZORBAX" column isocratic elution with 45/55 A/B (containing 0.1% TFA) at 40° C., detection at λ=210 nm. The reaction mixture was diluted with mobile then quenched by the addition of 1 mL of water. The volatiles were removed in vacuo to obtain a residue. The residue was purified by preparative HPLC (50/50 H$_2$O/CH$_3$CN, 15 mL/min, 21.2×250 "ZORBAX" C8, collecting 22.5 mL fractions λ=210,277 nm), combining the appropriate fractions and lyophilizing to obtain 56 milligrams (23 percent) of a white powder. The compound was characterized by $^{13}$C NMR, $^1$H NMR, IR (ν=2258 cm$^{-1}$, weak), 2D-NMR(COSY), UV and mass spectroscopy (M+Li=1020 amu) to be compound Ib with R$^I$ as 9,10-dimethyltridecyl (Seq. ID No. 12).

EXAMPLE V

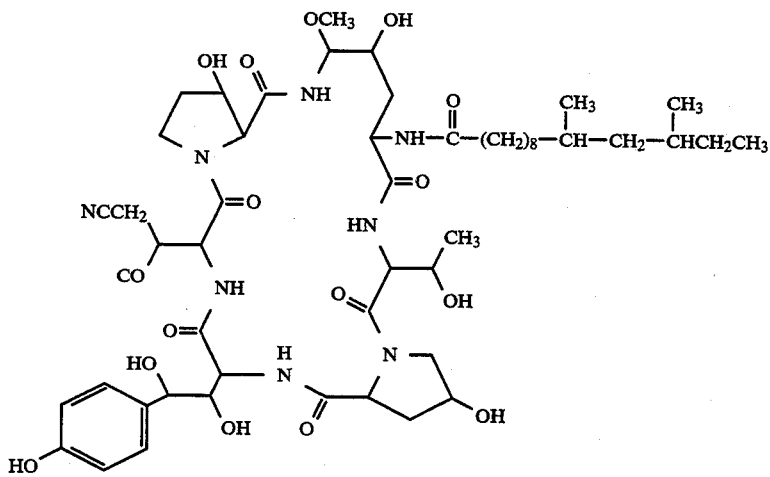

(Ic) Seq. ID No. 28

To a solution of 44 milligrams (42 μmol) of Compound Ia (Seq. ID No. 1) (prepared as described in Example I) in 2.0 milliliters of methanol is added 20 milligrams (2 eq) of camphorsulfonic acid and the resulting mixture is stirred at room temperature for three hours.

The reaction mixture is injected directly onto "ZORBAX" (25 mm×25 cm) C8 column and eluted with 50/50 A:B at 8.0 mL/min. The pure fractions as determined by HPLC are pooled and lyophilized to obtain Compound Ic. (Seq. ID No. 28).

EXAMPLE VI

The reaction mixture was diluted with 2.0 milliliters of 50 percent aqueous acetonitrile and injected onto a radial compression C18 Delta-Pak column (15μ, 100 A; 25 mm×50 cm). Elution was started at 12.0 mL/min. with 75:25 water/acetonitrile (0.1% TFA) until all the DMF and other front running materials had been eluted. The gradient was then stepped up to 50:50 over the course of 30 minutes and pure fractions of the product were collected, combined, and lyophilized to obtain 60 milligrams (55.5% yield) of product of >99.5% purity as determined by HPLC ("ZORBAX" C18; isocratic elution with 6:4 water/acetonitrile (0.1% TFA) 1.5 mL/min.; 40° C.; λ210 nm; retention time=9.74 min.). The product had the following spectral characteristics:

$^1$H-NMR (400 MHz; CD$_3$OD) δ 7.82 (d,2 H), 7.12 (d, 2 H) 6.94 (d, 2 H), 6.75 (d, 2 H), 5.37 (d, 1 H) 2.86 (dd, 1 H), 2.76 (dd, 1 H), 2.44 (m, 1 H), 2.29 (m, 1 H), 1.21 (d, 3 H), 0.9 (t, 3 H).

Mass Spectra (FAB) 1048 (M+Li)

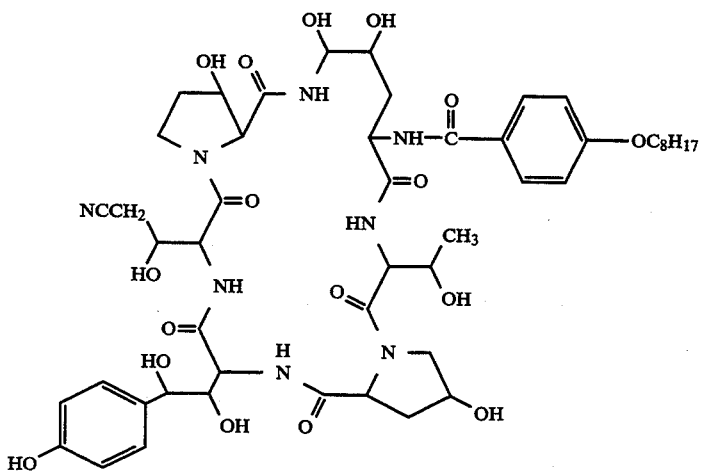

(Id) Seq. ID No. 1

To a solution of 110 milligrams (0.104 mmol) of a lipopeptide compound (R$_1$, R$_2$, R$_3$ and R$_4$ are OH, R$_5$ is H, R$_6$ is CH$_3$ and R$^I$ is C$_6$H$_4$OC$_8$H$_{17}$ Seq. ID. No. 1) in sieve-dried DMF under an atmosphere of nitrogen was added 59 milligrams (0.322 mmol) of cyanuric acid in one portion. The reaction was allowed to proceed for 5.5 minutes and then quenched by the addition of 1.35 milliliters of 2M sodium acetate solution. HPLC analysis showed a product to starting material ratio of 15.5:1.

EXAMPLE VII

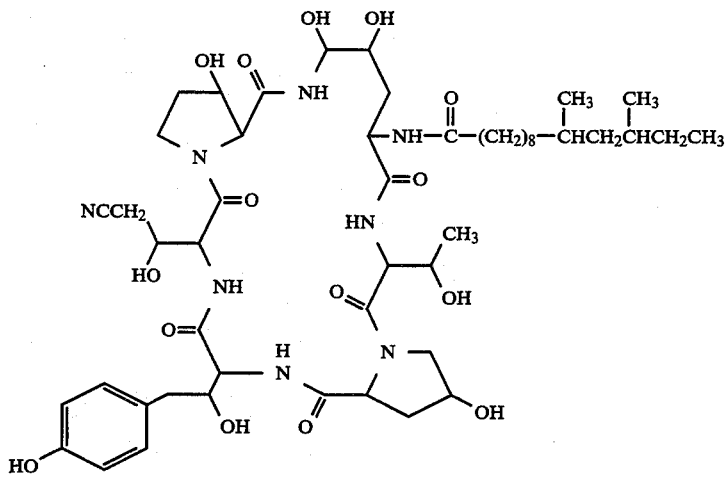

(Ie) Seq. ID. 27

The nitrile formula (Ia) prepared as described in Example I was employed as starting material for the preparation of a different nuclear configuration of formula (Ie)

Eleven milliliters of trifluoroacetic acid was added to 0.570 gram (0.544 mmol) of nitrile (Ia) and 1.10 grams (5.19 mmol) of sodium triacetoxyborohydride and the mixture stirred for 120 seconds to obtain a clear solution. The solution was poured into 150 milliliters of distilled water to obtain a precipitate which was recovered. The solid was purified by dissolving in a small amount of methanol, and adding just enough water to the point of precipitation and purified by preparative HPLC "ZORBAX" C18 and eluting with 53%A/47%B where A is 95% water/5% acetonitrile and B is 5% water/95% acetonitrile) and thereafter lyophilizing the appropriate fractions to obtain 0.220 gram of the desired compound. The product had the following spectral properties:

$^1$H-NMR (400 MHz; CD$_3$OD) δ 7.01 (d, 1H, J=10 Hz), 6.69 (d, 1H, 10 Hz), 5.33 (d, 1H, J=3 Hz), 5.06 (d, 1H, J=5 Hz) and 5.00 (d, 1H, J=4 Hz).

Mass Spectra: (FAB) 1038 (M+Li)

EXAMPLE VIII

Compound E-1 is cultivated with Actinoplanaceae to obtain a cyclopeptide nucleus compound which is acylated with an active ester to obtain a compound in which the side chain is varied. Thus modified compounds, in a manner similar to that described above, is dehydrated to obtain the following compounds:

| Nitrile Compound | R$_1$ | R$_2$ | R$_3$ | R$_4$ | R$_5$ | R$_6$ | R$^I$ | SEQ ID |
|---|---|---|---|---|---|---|---|---|
| If | OH | OH | OH | OH | H | CH$_3$ | C$_{13}$H$_{27}$ | 1 |
| Ig | OH | OH | OH | OH | H | CH$_3$ | C$_6$H$_4$OC$_8$H$_{17}$ | 1 |
| Ih | OH | OH | OH | OH | H | CH$_3$ | (CH$_2$)$_7$CH=CH(CH$_2$)$_7$CH$_3$ | 1 |
| Ii | OH | OH | OH | OH | H | CH$_3$ | C$_{10}$H$_6$OC$_8$H$_{17}$ | 1 |
| Ij | OH | OH | OH | OH | H | CH$_3$ | C$_{13}$H$_{27}$(n) | 1 |

EXAMPLE IX

In similar operations the following compounds may be prepared.

| Nitrile Compound | R$_1$ | R$_2$ | R$_3$ | R$_4$ | R$_5$ | R$_6$ | R$^I$ | SEQ ID |
|---|---|---|---|---|---|---|---|---|
| Ik | H | OH | H | OH | H | CH$_3$ | C$_{17}$H$_{25}$ | 12 |
| Il | H | OH | H | OH | H | CH$_3$ | (CH$_2$)$_7$CH=CH(CH$_2$)$_7$CH$_3$ | 12 |
| Im | H | OH | H | OH | H | CH$_3$ | C$_6$H$_4$OC$_8$H$_{17}$ | 12 |
| In | H | OH | H | OH | H | CH$_3$ | C$_{16}$H$_{33}$ | 12 |
| Io | H | OH | H | OH | H | CH$_3$ | C$_{10}$H$_6$OC$_8$H$_{17}$ | 12 |

EXAMPLE X 1000 compressed tablets each containing 500 mg of Compound Ia are prepared from the following formulation:

| Compound | Grams |
|---|---|
| Compound Ia (Seq. ID No. 1) | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE XI 1000 hard gelatin capsules, each containing 500 mg of Compound Ib are prepared from the following formulation:

| Compound | Grams |
| --- | --- |
| Compound Ib | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE XII

An aerosol composition may be prepared having the following formulation:

|  | Per Canister |
| --- | --- |
| Compound Ia | 24 mg |
| Lecithin NF Liquid Concentrated | 1.2 mg |
| Trichlorofluoromethane, NF | 4.026 g |
| Dichlordifluormethane, NF | 12.15 g |

EXAMPLE XIII 250 milliliters of an injectible solution may be prepared by conventional procedures having the following formulation:

| Dextrose | 12.5 g |
| --- | --- |
| 26% aqueous polyethylene glycol 300 | 250 ml |
| Compound Ib | 400 mg |

The ingredients are blended and thereafter sterilized for use.

Preparation of Starting Materials

The starting materials for the compounds are natural products or derivatives of natural products.

The following compounds are natural products produced by cultivating an appropriate organism in nutrient medium.

E-1 may be produced by cultivating *Zalerion arboricola* ATCC 20868 in a nutrient medium enriched in mannitol as the primary source of carbon as described in U.S. Pat. No. 5,021,341, Jun. 4, 1991.

E-2 may be produced by cultivating *Zalerion arboricola* ATCC 20868 in nutrient medium as described in U.S. Pat. No. 4,931,352, Jun. 5, 1990 or in nutrient medium enriched in glycerol as described in U.S. Pat. No. 4,968,608, Nov. 6, 1990.

E-2 nucleus with a different R may be produced by cultivating *Acrophialophora limonispora* in nutrient medium as described in U.S. Pat. No. 4,173,629.

E-3, E-10 and E-11 may be produced by cultivating *Cryptosporiopsis* ATCC 20594 in nutrient medium as described by Pache et al in 13th ICC (1983), PS 4.8/3, Part 115, Abstract No. 10 and PCT WO82/00587.

E-4, E-5 and E-6 may be produced by cultivating *Zalerion arboricola* ATCC 20868 in nutrient medium.

E-7 may be produced by cultivating *Zalerion arboricola* ATCC 20958 in nutrient medium as described in U.S. Pat. No. 5,021,403.

E-8 may be produced by cultivating *Zalerion arboricola* ATCC 20958 in nutrient medium.

E-9 may be produced by cultivating *Zalerion arboricola* ATCC 74030 in nutrient medium.

Starting materials which are cyclohexapeptides in which the nucleus of the foregoing has been modified to produce novel hexapeptides in which $R_3$ or both $R_3$ and $R_1$ are hydrogen instead of hydroxyl may be obtained by intimately mixing a compound in which $R_3$ is hydroxyl and $R_1$ may be hydroxyl with a reducing agent such as sodium cyanoborohydride in the presence of a strong acid such as trifluoroacetic acid and the mixture stirred until the reaction is complete. The volatiles are then removed under reduced pressure and the residue purified by reverse phase chromatography employing water/acetonitrile to obtain a purified product. When $R_1$ is OH and it is desired to reduce only $R_3$, essentially the same procedure is used except that the reactant lipopeptide is first dissolved in glacial acetic acid and the reaction carried out in a similar manner. A compound in which $R_1$ and $R_3$ are H, and $R_2$ and $R_4$ are OH, $R_5$ is H and $R_6$ is $CH_3$ may be identified as E-12 and a compound in which $R_3$ is H and $R_1$, $R_2$ and $R_4$ are OH, $R_5$ is H and $R_6$ is $CH_3$ may be identified as E-13.

Starting materials in which $R^I$ is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as also described in Experientia 34, 1670 (1978) or U.S. Pat. No. 4,293,482, and thereafter recovering the deacylated cyclopeptide, and acylating the deacylated cyclopeptide by mixing together with an appropriate active ester $R^I COX$ to obtain Compound E with the desired acyl group as also described in U.S. Pat. Nos. 4,287,120 and 4,293,489.

When $R_1$ is H, $R_2$, $R_3$ and $R_4$ are OH, $R_5$ is H or $CH_3$ and $R_6$ is $CH_3$, the nitrile intermediate may be made using another nitrile compound, in which $R_1$ is OH with the remaining $R_5$ being the same, and reducing $R_1$ by methods known to the skilled in the art. Conveniently this may be carried out by adding trifluoroacetic acid to the nitrile and triacetoxyborohydride and mixing together until a clear solution is obtained and thereafter recovering the product as a precipitate by pouring into water. The precipitate product may then be purified by preparative HPLC by placing on the column in a methanol/water mixture eluting with water/acetonitrile.

What is claimed is:
1. A compound having the formula:

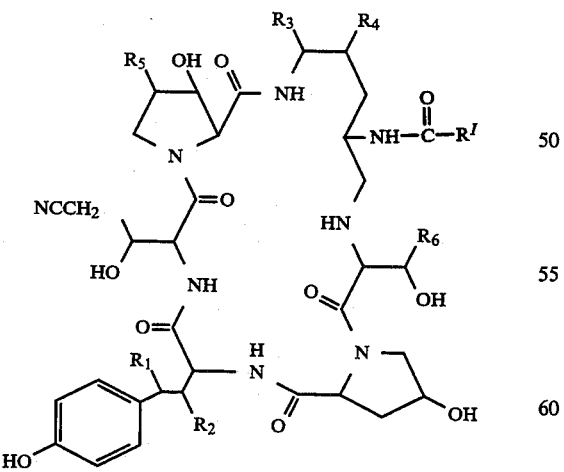

wherein
  $R_1$ is H or OH
  $R_2$ is H or OH
  $R_3$ is H, OH or OR where R is $C_1$–$C_4$ alkyl or benzyl
  $R_4$ is H or OH
  $R_5$ is H, OH or $CH_3$
  $R_6$ is H or $CH_3$, and
  $R^I$ is $C_9$–$C_{21}$ alkyl, $C_9$–$C_{21}$ alkenyl, $C_1$–$C_{10}$ alkoxyphenyl, or $C_1$–$C_{10}$ alkoxynaphthyl.

2. A compound according to claim 1 having the formula

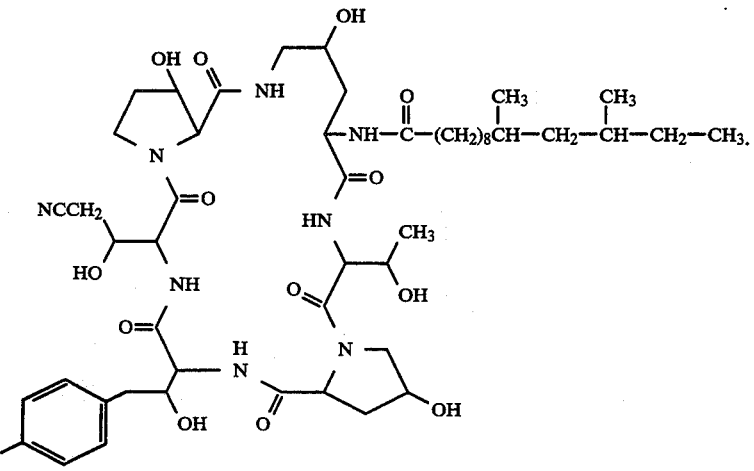

3. A compound according to claim 1 having the formula:

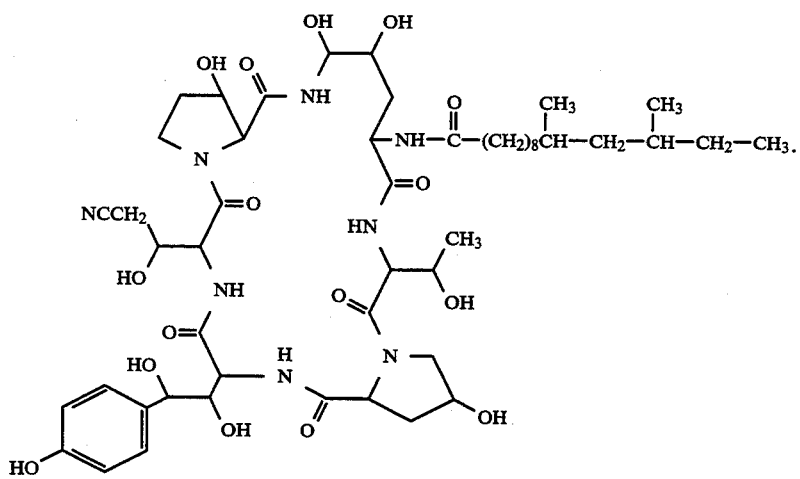
4. A compound according to claim 1 having the formula:
5. A compound according to claim 1 having the formula
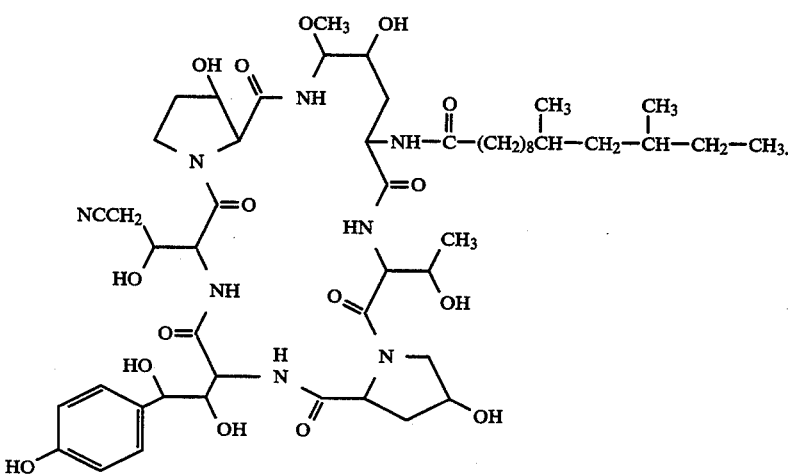
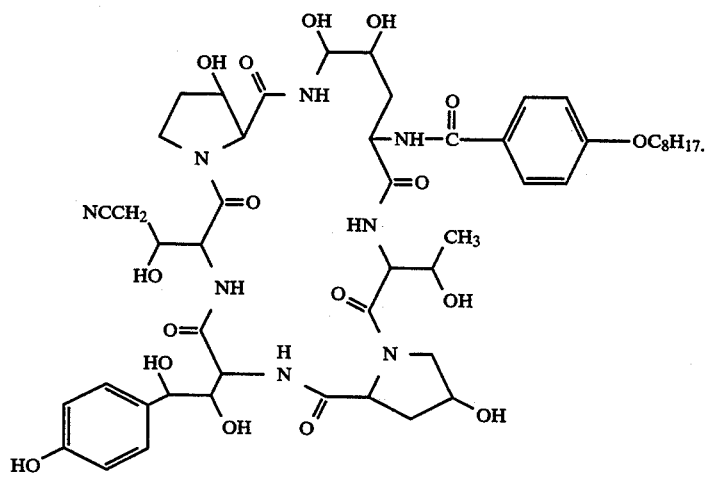
6. A compound according to claim 1 having the formula

7. A compound according to claim 1 having the formula
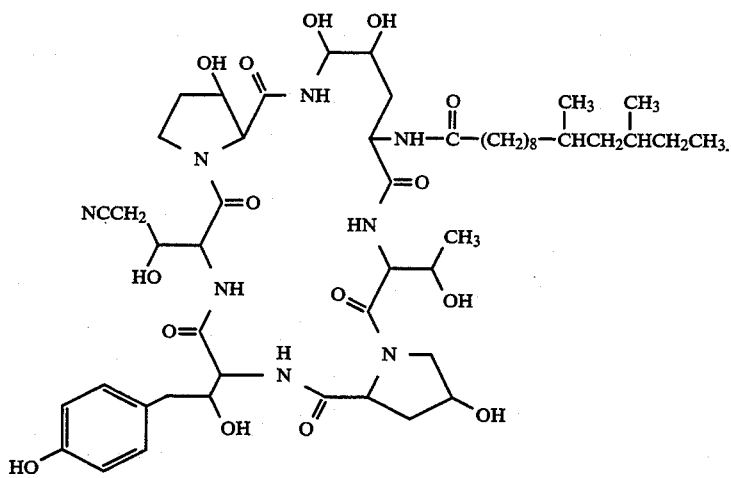
8. An antibiotic composition comprising a therapeutic amount of a compound of claim 1 in a pharmaceutically acceptable carrier.
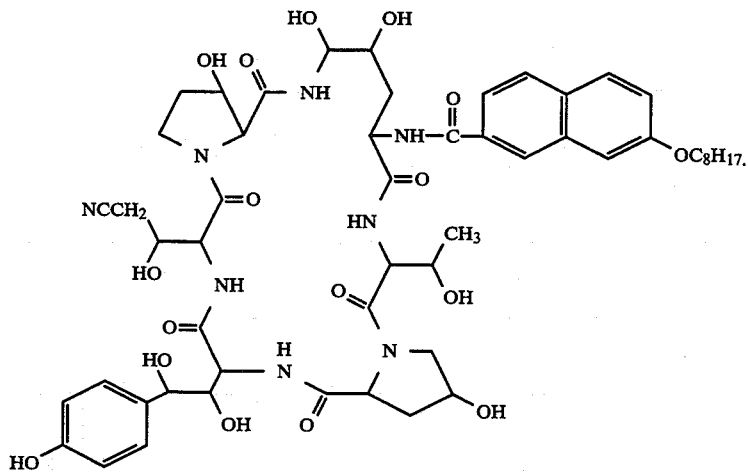
9. A composition according to claim 8 in unit dosage form wherein the compound of claim 1 is present in an amount of 100 to 200 milligrams.
* * * * *